United States Patent
Sumanaweera et al.

(10) Patent No.: US 6,234,968 B1
(45) Date of Patent: May 22, 2001

(54) 3-D DIAGNOSTIC MEDICAL ULTRASOUND IMAGING USING A 1-D ARRAY

(75) Inventors: Thilaka S. Sumanaweera, San Jose; Mirsaid Bolorforosh; John A. Hossack, both of Palo Alto, all of CA (US)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 09/333,823

(22) Filed: Jun. 15, 1999

(51) Int. Cl.[7] ................................................. A61B 8/00
(52) U.S. Cl. ............................................................ 600/443
(58) Field of Search ................................ 600/443, 916, 600/447; 73/625–626

(56) References Cited

U.S. PATENT DOCUMENTS

| | | | |
|---|---|---|---|
| Re. 35,720 | 2/1998 | Arenson | 128/660.05 |
| 5,148,810 | 9/1992 | Maslak | 128/661.01 |
| 5,235,986 | 8/1993 | Maslak | 128/661.01 |
| 5,261,408 | 11/1993 | Maslak | 128/661.01 |
| 5,353,354 | 10/1994 | Keller | 382/6 |
| 5,396,890 | 3/1995 | Weng | 128/660.07 |
| 5,398,691 | 3/1995 | Martin | 128/660.06 |
| 5,454,371 | 10/1995 | Fenster | 128/660.07 |
| 5,474,073 | 12/1995 | Schwartz | 128/661.1 |
| 5,575,286 | 11/1996 | Weng | 128/653.1 |
| 5,608,849 | * 3/1997 | King, Jr. | 600/443 |
| 5,655,535 | 8/1997 | Friemel | 128/660.07 |
| 5,709,206 | * 1/1998 | Teboul | 600/437 |
| 5,776,067 | * 7/1998 | Kamada et al. | 128/916 X |
| 5,901,708 | * 5/1999 | Chong et al. | 128/916 |
| 5,916,168 | * 6/1999 | Pedersen et al. | 128/916 |
| 5,993,390 | * 11/1999 | Savord et al. | 600/437 |

* cited by examiner

*Primary Examiner*—Francis J. Jaworski
(74) *Attorney, Agent, or Firm*—Brinks Hofer Gilson & Lione

(57) ABSTRACT

A method and apparatus to collect a 3-D volume of data using a generic 1-D ultrasound transducer, without using special fixtures, such as position tracking hardware. A 3-D volume is generated by performing two data collecting sweeps, or alternatively, by collecting data from a plurality of locator planes (non-coplanar intersecting planes) and performing one data collecting sweep or rotation. Lines of intersection are determined from intersecting planes of 2-D data sets collected from the 1-D ultrasound transducer. The 2-D data sets are assembled into a 3-D data set and scan converted in a 3-D grid for display.

112 Claims, 8 Drawing Sheets

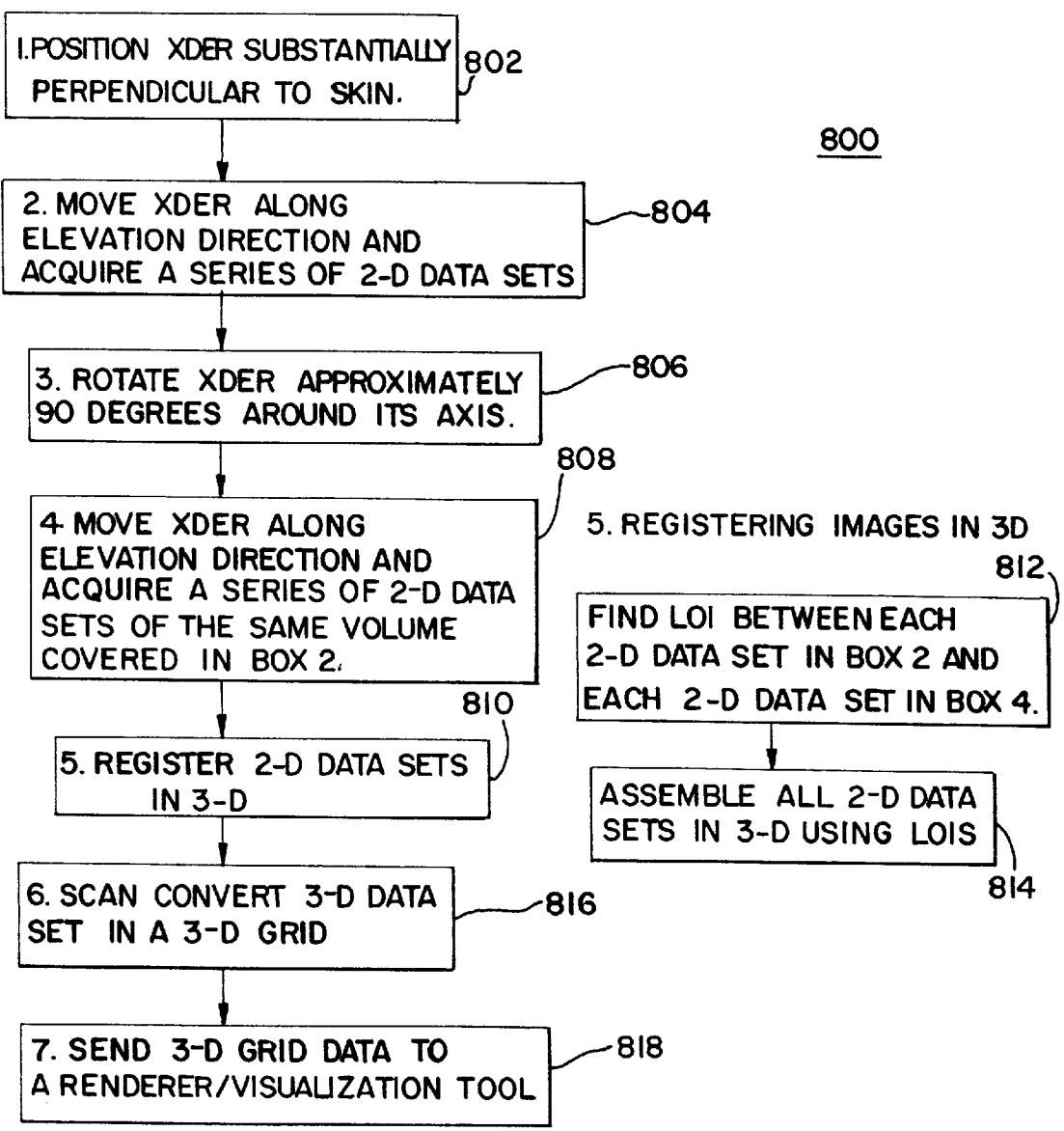

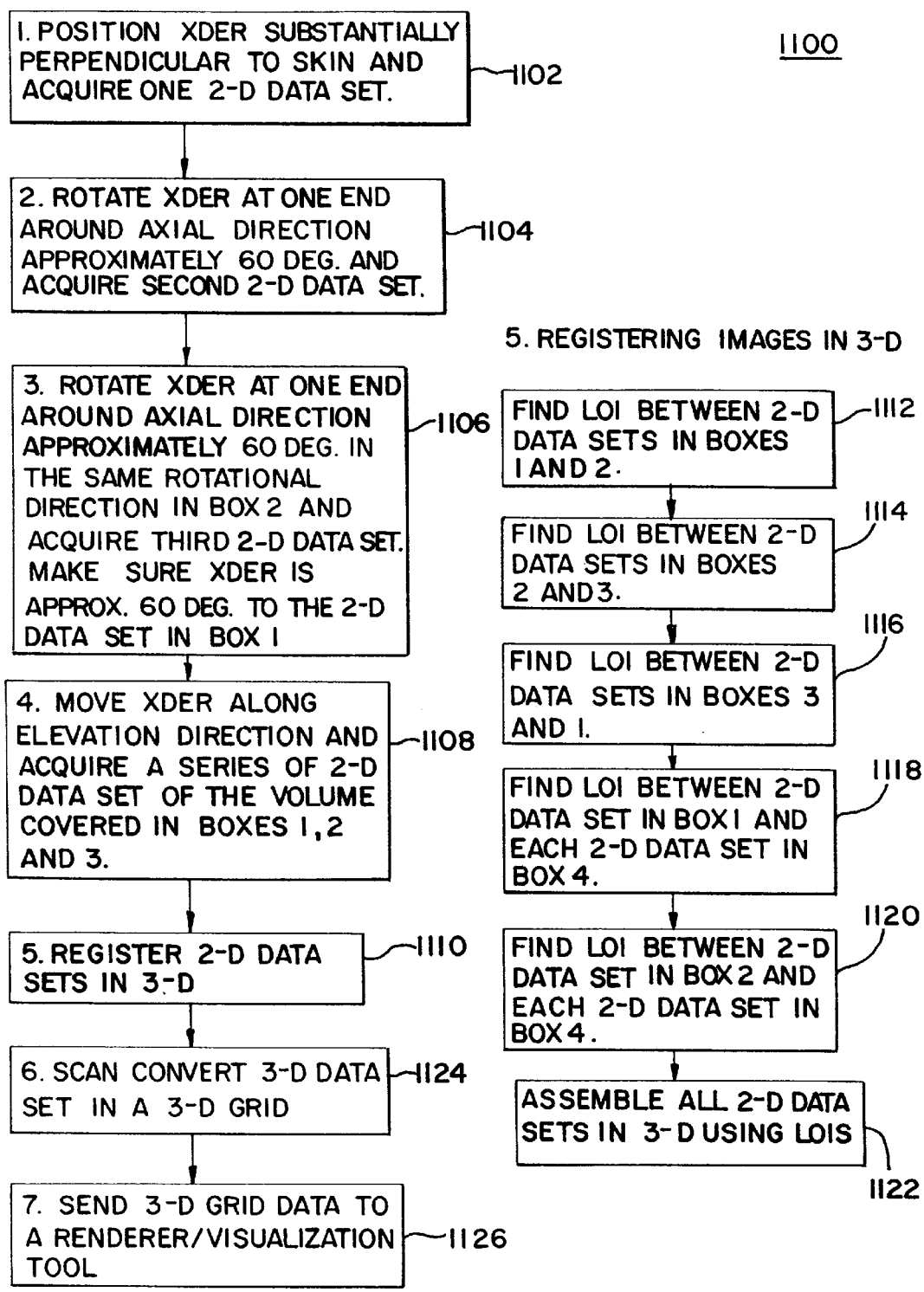

3-D DIAGNOSTIC MEDICAL ULTRASOUND IMAGING USING A 1-D ARRAY

BACKGROUND OF THE INVENTION

1. Field of the Invention

This invention relates generally to developing accurate 3-D diagnostic medical ultrasound volume data from information acquired from scanning a human or animal body with a 1-D ultrasound transducer.

2. Description of the Prior Art

There are several methods in the prior art for gathering 3-D ultrasound volume data using a 1-D ultrasound transducer. These methods typically involve moving a 1-D ultrasound transducer with a linear array of elements over the surface of the 3-D volume in the elevation direction (perpendicular to both the long axis of the linear array and the vertical direction into or out of the surface being scanned). A 3-D volume is generated, based on assuming a particular motion of the transducer. As a result, the 3-D volume is qualitative rather than quantitative, making the data inadequate for measurement of various parameters such as distances, areas, and volumes.

There are also several quantitative methods in the prior art as well. Some prior art methods use mechanical position sensors to detect the relative positions of the 1-D ultrasound transducer. Other prior art methods use a magnetic position sensor or a precision motor to move the transducer along the elevation direction by precise translational increments to achieve the same objective. The position sensing methods require additional hardware, making the ultrasound transducer more specialized, unwieldy, and costly.

The prior art also discloses using a variety of parameters (e.g., timing delay, spectral breadth, spectral power and the speckle de-correlation coefficient) to estimate the elevation motion of a 1-D ultrasound transducer without using additional hardware. While this method is less costly and simpler to use, the accuracy of position estimation of the transducer may not be adequate for quantitative measurements due to limitations inherent in the methods, such as direction ambiguity due to symmetric correlation functions.

A method has been disclosed for generating a spatially accurate 3-D data set from a series of 2-D data sets from an ultrasound transducer modified to incorporate multiple arrays. This method is described in co-pending U.S. patent application Ser. No. 08/916,585, filed on Aug. 22, 1997, entitled "Multiple Ultrasound Image Registration System, Method and Transducer," which is assigned to the assignee of the present invention.

What is needed is a method for generating a spatially accurate 3-D ultrasound data set using a 1-D single array ultrasound transducer without any modifications or the addition of position sensing hardware.

SUMMARY OF THE INVENTION

An object of the present invention is to provide a system and method for generating a spatially accurate 3-D ultrasound data set using input from a 1-D single array ultrasound transducer without any modifications or the addition of position sensing hardware.

The invention is directed to using two intersecting sets of 2-D ultrasound data planes as the input for creating a 3-D volume. The lines of intersection for pairs of non-coplanar (intersecting) 2-D ultrasound data sets are found. The lines of intersection are then used to assemble the 2-D ultrasound data sets into a 3-D ultrasound data set.

These and other objects and advantages of the invention will become apparent to those skilled in the art from the following detailed description of the invention and the accompanying drawings.

BRIEF DESCRIPTION OF THE DRAWINGS

FIG. 3($c$) is a view of the line of intersection of two non-coplanar 2-D data sets.

FIG. 3($d$) is a 3-D reconstruction of four 2-D data sets using the lines of intersection.

FIG. 6($b$) is a view of the triangular prism of FIG. 6($a$) along the z-axis.

FIG. 7($b$) is a perspective view of an alternative scanning protocol with three non-coplanar locator planes (A, B, and C) and the rotation of a transducer around its axis.

FIG. 7($c$) is a perspective view of an alternative scanning protocol with three non-coplanar locator planes (A, B, and C) forming a triangular prism and the movement of a transducer along its elevation direction.

FIG. 8 is a flowchart of the method used for the scanning protocol for FIGS. 3($a$) and 3($b$).

FIG. 11 is a flowchart of the method used for the scanning protocol for FIG. 7($c$).

DETAILED DESCRIPTION OF THE PREFERRED EMBODIMENTS

The invention is generally directed to a system and method to collect a 3-D volume of diagnostic medical ultrasound data using input from a transducer scanning a body (human or animal), without requiring transducer modification and without using special fixtures, such as position tracking hardware.

Two sets of 2-D ultrasound data can be obtained in a variety of ways using an ordinary transducer. For example, a 1-D ultrasound transducer is moved along its elevation direction while acquiring a first series of 2-D data sets. The position and orientation of the transducer is then changed and the transducer is then moved along its elevation direction once more while acquiring a second series of 2-D data sets. The 3-D volume covered by the first and the second series of 2-D data sets is roughly the same. The line of intersection (LOI) of a 2-D data set from the first series and a 2-D data set from the second series (i.e., the line common to the two 2-D data sets) is found by correlating speckle or image features. After determining the LOI of each pair of 2-D data sets, a 3-D ultrasound data set is generated by assembling the 2-D data sets from the two series. Then the 3-D ultrasound data set is scan converted in a 3-D grid.

Alternatively, the first series of 2-D data sets is acquired by rocking the 1-D ultrasound transducer around its line of contact with the object. Then the second series of 2-D data sets is acquired either by transducer movement in the elevation direction, or by rotating the transducer around its axial direction.

In yet another alternative, the first series of 2-D data sets consists of three 2-D data sets acquired by rotating the transducer around its axial direction at one end of the transducer. The three 2-D data sets form a triangular prism in 3-D. Again, the second series of 2-D data sets is acquired either by transducer movement in the elevation direction, or by rotating the transducer around its axial direction.

The acquired 2-D data sets can be either acoustic data (ultrasound data obtained from the signal path before scan conversion) or image data (post scan conversion data). Various ultrasound systems are capable of acquiring 2-D data sets from a 1-D or 1.5-D ultrasound transducer as detailed below.

Figure 1:
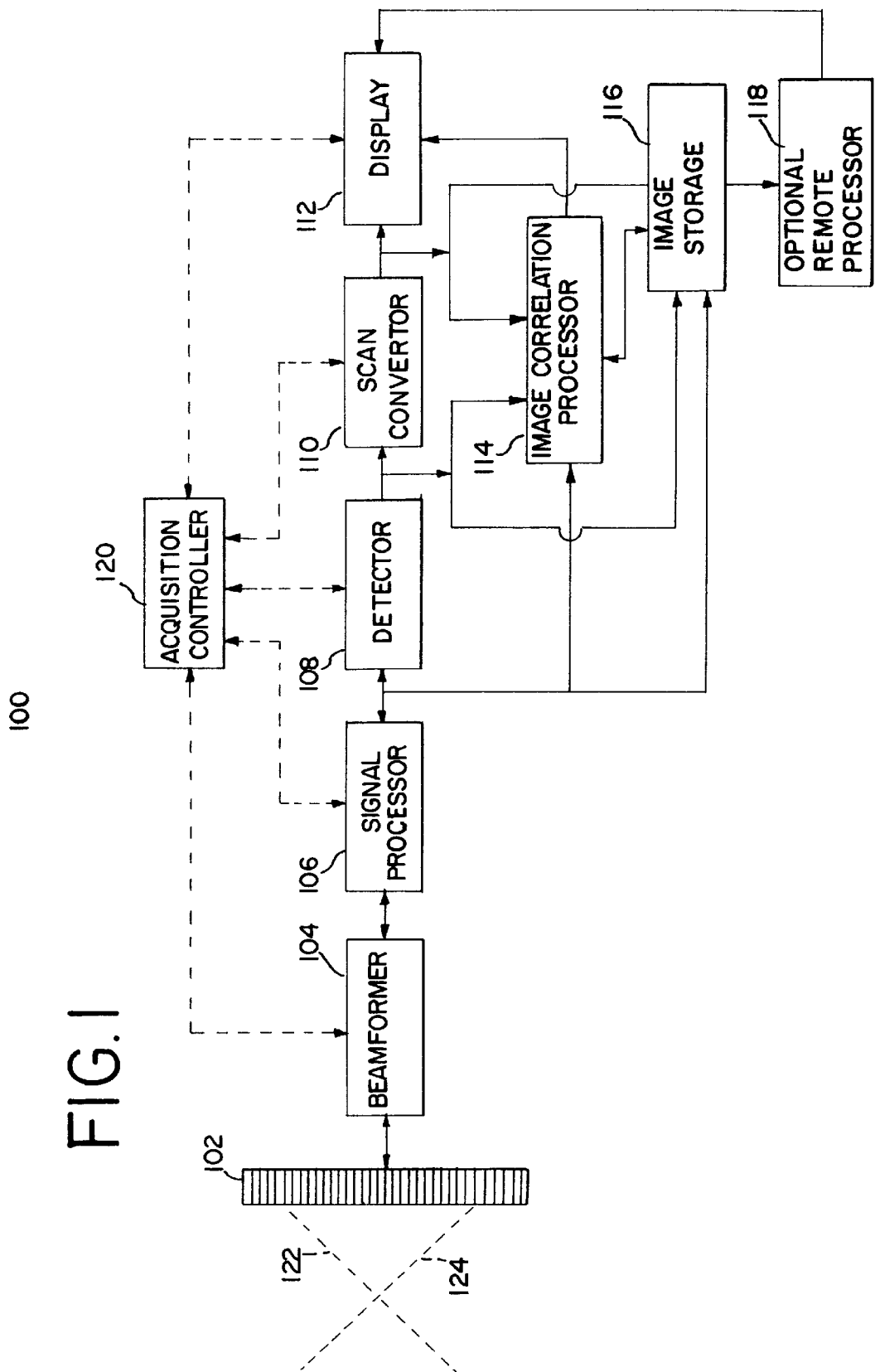
FIG. 1 is a schematic block diagram of an ultrasound imaging system.

One embodiment of an ultrasound system 100 is shown schematically in FIG. 1. System 100 includes a data path comprising transducer 102, beamformer 104, signal processor 106, detector 108, scan converter 110, display device 112, image correlation processor 114, image storage 116 and optional remote processor 118. Acquisition controller 120 directly outputs control signals and receives status signals for the control of beamformer 104, signal processor 106, detector 108, scan converter 110, and display device 112. Image correlation processor 114 is connected to the data path, preferably receiving inputs from the output lines of signal processor 106, detector 108, scan converter 110, and image storage 116. Image correlation processor 114 produces output data which is received by display device 112 and image storage 116. Image storage 116 receives input data from the output lines of signal processor 106, detector 108, scan converter 110, and image correlation processor 114, and outputs data to optional remote processor 118. Optional remote processor 118 outputs data to display device 112.

Transducer 102 is typically a phased linear array of piezoelectric elements. Beamformer 104 is constructed in a manner known in the art. Beamformer 104 may optionally comprise separate transmit and receive beamformers. Beamformer 104 produces excitation signals for each or a subset (i.e., a sub-aperture) of the elements of transducer 102. The excitation signals are processed, such as by applying a relative delay or amplitude, to focus ultrasound waveforms along one or more scan lines 122 and 124. The scan lines can be at any of various angles relative to transducer 102 and originate at various locations along, in front of, or behind transducer 102. Variable origin and variable angle acoustic scanning methods and apparatus (which generate Vector® wide view array imaging formats) are disclosed in U.S. Pat. No. 5,148,810, U.S. Pat. No. 5,235,986, and U.S. Pat. No. 5,261,408 to Maslak, et al., which are assigned to the assignee of the present invention and hereby incorporated by reference. The plane defined by two or more scan lines comprises a scan plane.

The acoustic waveforms are reflected off of structures within a body as echoes, which are detected by the elements of transducer 102 and provided as voltage signals to beamformer 104. Beamformer 104 sums the voltage signals and outputs ultrasound data representative of structures along the one or more scan lines.

Signal processor 106 is a construction known in the art, such as a digital signal processor or filtering device for processing the representative ultrasound data. Signal processor 106 can include a B-mode processor and/or a spectral Doppler processor. Alternatively or in addition, signal processor 106 can estimate the Doppler velocity, energy, and/or variance for each of various points along each scan line; or it can estimate Doppler tissue velocity, energy or acceleration, as described in Reissued U.S. Pat. No. 35,720 to Arenson, et al. Sequences of the B-mode and/or Doppler acoustic or image frame data can be stored in image storage 116.

In a preferred embodiment, signal processor 106 also supports harmonic imaging, i.e., harmonic B-mode images or harmonic color Doppler images, wherein the received acoustic data is at a harmonic frequency of the transmitted acoustic pulses. Harmonic color Doppler images superimpose the image of moving blood, in color, on a real-time grayscale B-mode display. Turbulence, direction, and speed of blood flow are indicated by appropriate colors.

The acoustic data representing areas in the scan plane or along a scan line is provided by signal processor 106 to detector 108 and scan converter 110. Scan converter 110 is a processor or a dedicated circuit for formatting the acoustic data into a Cartesian coordinate system for display as images. For each grid point in the Cartesian coordinate system, the nearest acquired sample data points are interpolated to find the data value corresponding to each grid point. The interpolation algorithm can use a linear or higher order function, such as a higher order polynomial function.

Display device 112 is a monitor, such as a color monitor. The scan converted data representing the scan plane is displayed on display device 112 based on B-mode intensity, Doppler velocity, Doppler energy, Doppler variance, Doppler tissue velocity, energy, or acceleration, spectral Doppler or any combination thereof, and in any combination of fundamental and/or harmonic imaging.

Image correlation processor 114 is a digital signal processor or multi-purpose processor for calculating the 3-D volumes from the 2-D data sets. Image correlation processor 114 obtains or stores orientation information corresponding to the various scan lines or Cartesian coordinates. The calculated 3-D volumes are provided to display device 112. Preferably, the calculated information is displayed within 10 seconds or displayed at least within 60 seconds from completion of the acquisition of at least two 2-D data sets.

In an alternative embodiment, image correlation processor 114 is integrated with the ultrasound signal path, especially if image correlation processor 114 has the additional capability of performing the functions of signal processor 106. Alternatively, the functions of image correlation processor 114 are performed by remote processor 118, a separate, stand-alone processor (e.g., a personal computer or workstation).

The acquisition controller 120 provides control instructions to various elements of system 100. For example, acquisition controller 120 controls beamformer 104 to generate acoustic waveforms along scan lines 122 and 124 in certain directions and scan formats. Alternatively, a separate processor provides control of system 100. Image correlation processor 114, acquisition controller 120 or another processor may also coordinate user input.

Figure 2:
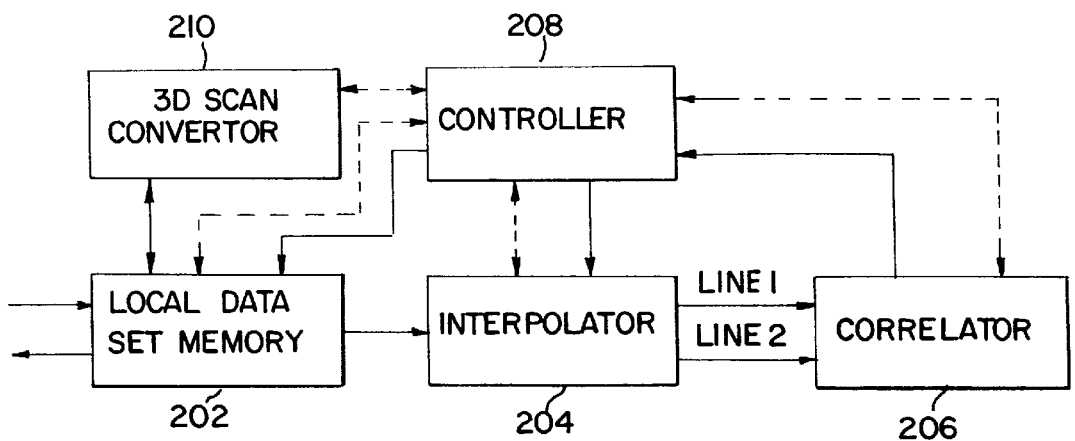
FIG. 2 is a schematic block diagram of an image correlation processor.

FIG. 2 shows a preferred hardware implementation of image correlation processor 114. Image correlation processor 114 is connected to the data path through local data set memory 202, preferably receiving inputs from the output lines of signal processor 106, detector 108, scan converter 110, and image storage 116 (see FIG. 1). Image correlation processor 114 produces output data through local data set memory 202, which is received by display device 112 and image storage 116. Local data set memory 202 holds incoming data sets. Controller 208 then computes the data line origins and angles of the lines of data to be correlated. These computed parameters are then fed as inputs to interpolator 204, which interpolates the incoming data sets to produce two lines of data, line 1 and line 2. These lines of data are then sent to correlator 206, which correlates the two lines. The correlation coefficient is then sent back to controller 208. Controller 208 sends the next set of origins and angles to interpolator 204. The process repeats until all possible line origins and angles are exhausted. Controller 208 then sends the origins and angles of the lines of data corresponding to the minimum correlation coefficient to local data set memory 202. 3-D scan converter 210 then converts the 3-D data set in a regular 3-D grid using the original 2-D data sets and the origin and angle data. The final data is sent back to local data set memory 202. Controller 208 also sends and receives control signals from 3-D scan converter 210, local data set memory 202, interpolator 204, and correlator 206.

Data Acquisition

Figure 3A:
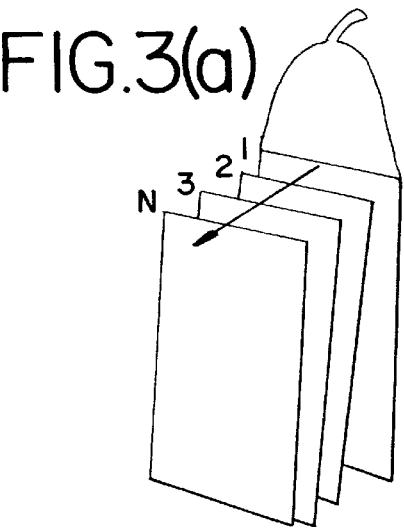
FIGS. 3($a$) and 3($b$) are perspective views of a 3-D volume generated by performing two sweeps of a 1-D ultrasound transducer along its elevation direction.

In FIG. 3(a), a 1-D ultrasound transducer is moved along its elevation direction while acquiring a series of 2-D data sets 1, 2, 3 . . . N; these 2-D data sets need not be parallel. The transducer could also be a 2-D ultrasound transducer acquiring a single plane at a time. The scan format can be linear, sector, Vector® wide view, curvilinear or curved Vector® wide view. Following this acquisition, the transducer is rotated approximately 90 degrees around its axial direction. A second set of 2-D data sets 1, 2, 3 . . . M is acquired by again moving the transducer along its elevation direction (see FIG. 3(b)), approximately covering the same volume covered by the previous series of 2-D data sets.

Registration of 2-D Data Sets in 3-D

The two series of 2-D data sets are processed to generate a 3-D volume of data, which is hereinafter termed "registration." Registration includes two steps: (a) determination of the lines of intersection and (b) assembly of the 2-D data sets in a common 3-D coordinate system.

Figure 3B:
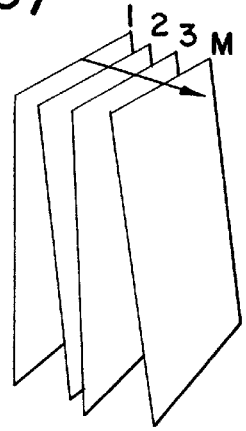
Figure 3C:
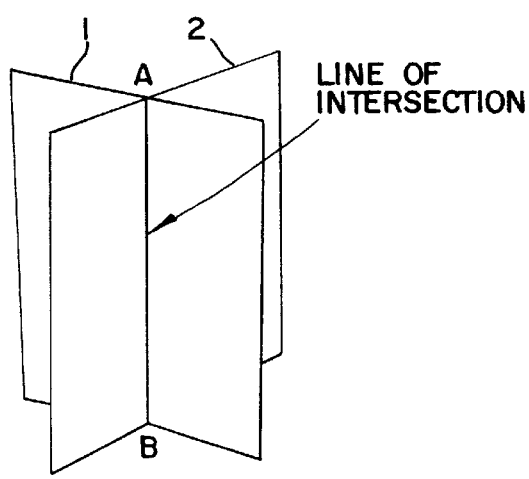
Figure 3D:
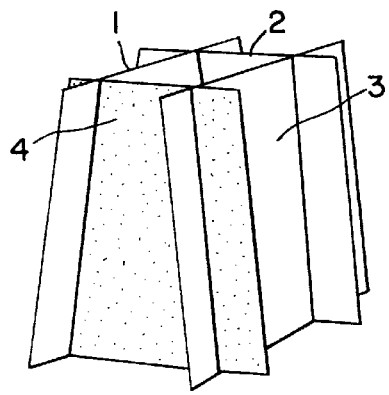

Consider the ultrasound 2-D data sets 1 and 2 shown in FIG. 3(c). The two 2-D data sets are non-coplanar and therefore intersect each other along a line of intersection, called AB. Once all the lines of intersection between the 2-D data sets from series (a) and series (b) are determined, all the 2-D data sets are fixed in 3-D space, thus generating a 3-D data set. This step is hereinafter termed, "assembly" of 2-D data sets. It must be assumed that one frame (e.g., the first frame) defines the origin and axes of the 3-D volume, since there is no absolute reference point or origin. FIG. 3(d) shows one such 3-D reconstruction of four non-coplanar 2-D data sets 1, 2, 3,and 4 using the lines of intersection.

Determination of the Line of Intersection

Figure 4:
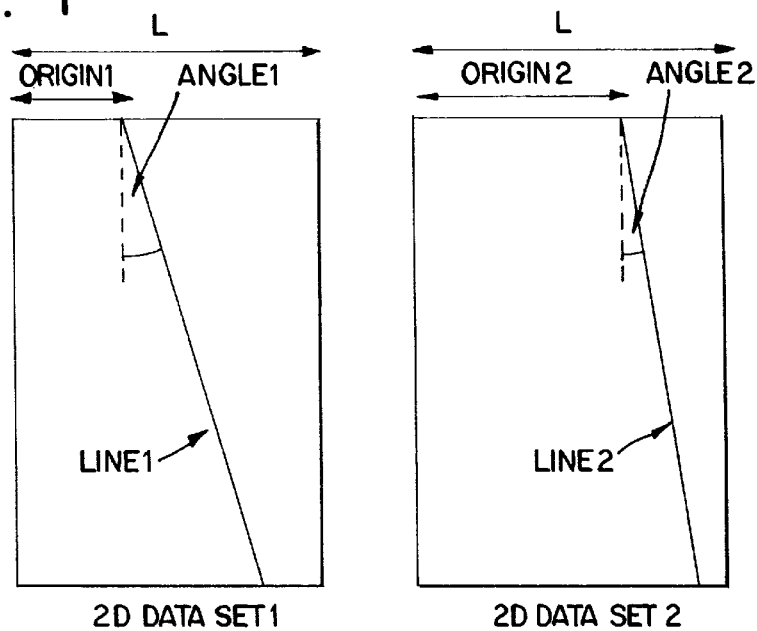
FIG. 4 shows the geometry used while finding the lines of intersection.

The LOI between two 2-D data sets is found by maximizing the cross-correlation coefficient of ultrasound line data from each 2-D data set. FIG. 4 shows how this is done for a linear scan format. Other scan formats can also be similarly accommodated. FIG. 4 shows a line from 2-D data set 1, line 1, and a line from 2-D data set 2, line 2. These lines may or may not include ultrasound lines along which acoustic pulses are sent. In fact, one of the above lines may include data gathered using multiple ultrasound lines. Line 1 is at a distance, origin1, away from the left edge of 2-D data set 1, making an angle, angle1, to the vertical axis. Similarly, line 2 is at a distance, origin2, away from the left edge of 2-D data set 2, making an angle, angle2, to the vertical axis. The algorithm for finding the LOI is summarized by the following pseudo-code:

```
maxOrigin1 = 0;
maxOrigin2 = 0;
maxAngle1 = 0;
maxAngle2 = 0;
max = findCrossCorrCoeff[2DDataSet1(maxOrigin1,maxAngle1),
    2DDataSet2(maxOrigin2, maxAngle2)];
for each origin1 in [0, L] in 2DDataSet1
  for each angle1 in [-ang, ang] in 2DDataSet1
    for each origin2 in [0, L] in 2DDataSet2
      for each angle2 in [-ang, ang] in 2DDataSet2
        val = findCrossCorrCoeff[2DDataSet1(origin1, angle1),
        2DDataSet2(origin2, angle2)];
        if (val > max)
            max = val;
            maxOrigin1 = origin1;
            maxOrigin2 = origin2;
            maxAngle1 = angle1;
            maxAngle2 = angle2;
      end
    end
  end
end
end
```

The values for origin1 and origin2 range from 0 to L, where L is the width of each 2-D data set. The values for angle1 and angle2 range from −ang to +ang, where ang is a preset angle. The incremental steps for each parameter, origin1, angle1, origin2, and angle2, are chosen to achieve a given localization accuracy.

The function, findCrossCorrCoeff, finds the cross-correlation coefficient between line 1 and line 2. Let lines 1 and 2 be represented by two series of regularly-spaced data samples: $l_i$ and $m_i$ (where i=1 . . . n). Then the cross-correlation coefficient, $C_{lm}$, is given by:

$$C_{lm} = \{\Sigma(l_i - l_{AVE})(m_i - m_{AVE})\} / \sqrt{\{\Sigma(l_i - l_{AVE})^2 \Sigma(m_i - m_{AVE})^2\}} \quad (1)$$

where $$l_{AVE} = (1/n)\Sigma l_i \text{ and } m_{AVE} = (1/n)\Sigma m_i$$

Figure 5:
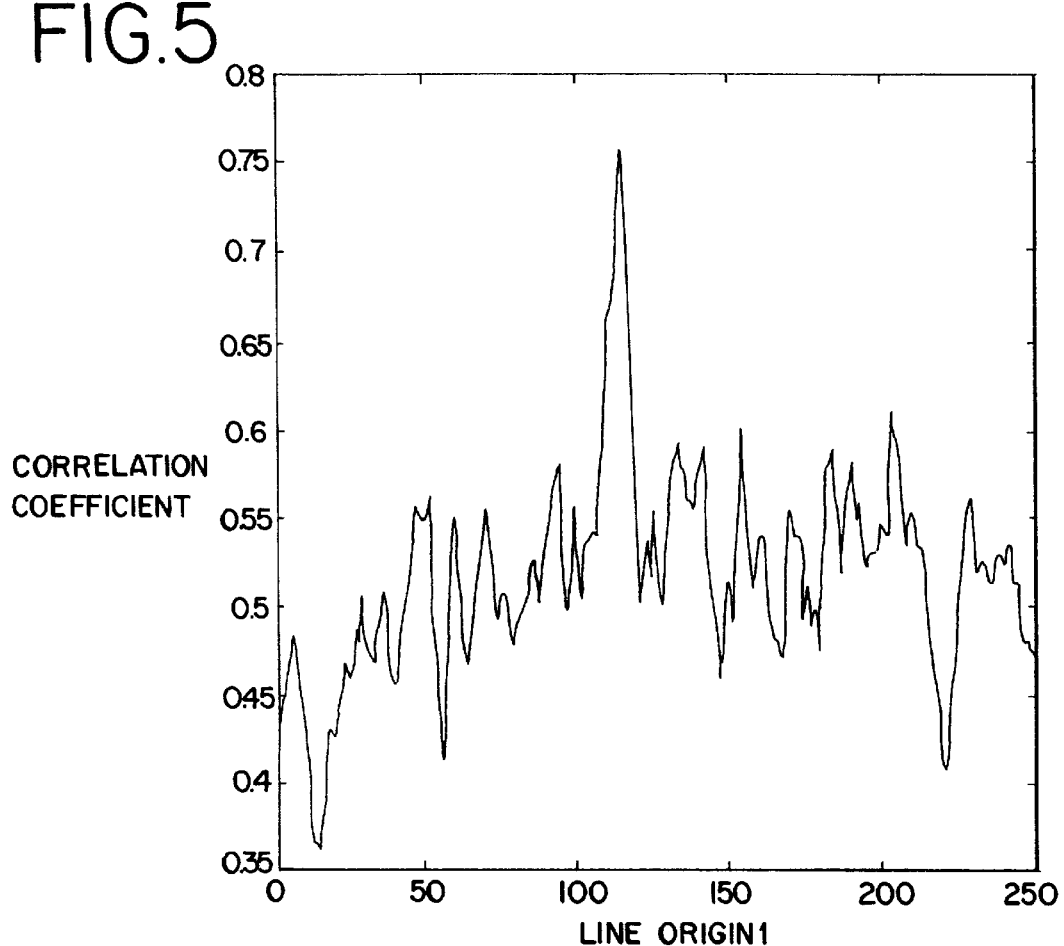
FIG. 5 is a graph of the correlation coefficient as a function of line origin.

The above pseudo-code computes the cross-correlation coefficient for each origin1, angle1, origin2 and angle2. It finds maxOrigin1, maxAngle1, maxOrigin2 and maxAngle2 corresponding to the maximum cross-correlation coefficient. FIG. 5 shows a representative 1-D plot of the cross-correlation coefficient as a function of origin1, where angle1=maxAngle1, origin2=maxOrigin2 and angle2=maxAngle2, demonstrating the behavior of the correlation surface near the maximum. The two 2-D data sets, in this case, were acquired by rotating a 1-D ultrasound transducer around its axial direction by approximately 90 degrees. Note that the peak correlation coefficient is about 0.75, demonstrating that the lines corresponding to LOI are well correlated.

Alternate methods to find the LOI are to maximize the product, (i.e., $\Sigma l_i m_i$), minimize the sum of squared differences (i.e., $\Sigma(l_i - m_i)^2$), or minimize the sum of absolute differences (i.e., $\Sigma|l_i - m_i|$). The lines of data may or may not be along ultrasound lines, but are derived from the 2-D data set, represented by the two series of regularly-spaced data samples, $l_i$ and $m_i$ (where i=1 . . . n). The samples can be detected and scan converted ultrasound data (i.e., image data), or data generated by combining adjacent raw complex number samples from the demodulated signals.

In an alternate embodiment of the invention, instead of finding lines of intersection between two 2-D data sets, two or more points of intersection are determined. The lines of intersection are then determined by using the lines best connecting the points of intersection. Alternatively, a multitude of segments of the lines of intersection are determined. The lines of intersection are then the lines best connecting the multitude of line segments.

Assembly of 2-D Data Sets in 3-D

Figure 6A:
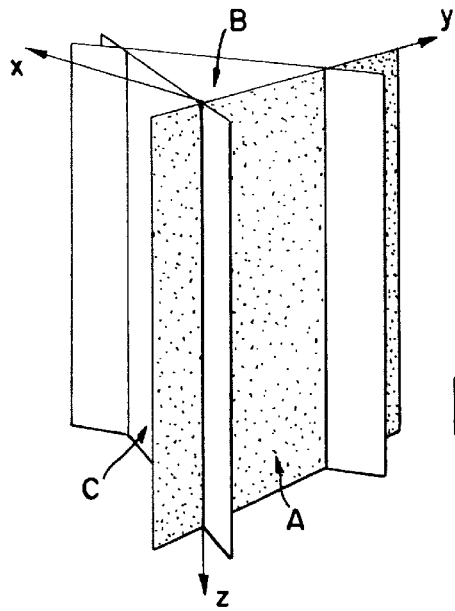
FIG. 6($a$) is a perspective view of three non-coplanar locator planes (A, B, and C).

Once the lines of intersection of pairs of 2-D data sets are determined, the 2-D data sets can be assembled in 3-D space as follows. For simplicity, let us consider the scanning protocol shown in FIG. 7(c). FIG. 6(a) shows the three locator planes, A, B, and C, of this scanning protocol forming a triangular prism. For simplicity, again, let these planes be normal to the object surface. In this case, the lines of intersections are perpendicular to the object surface.

Figure 6B:
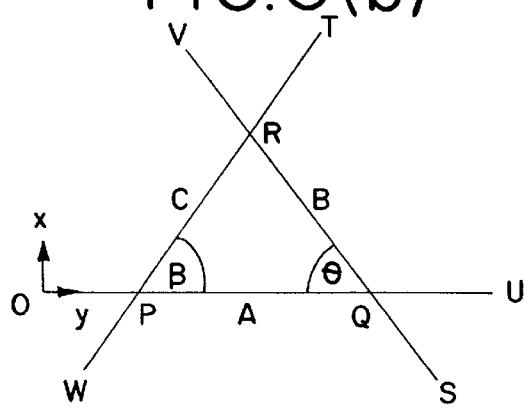

Let the coordinate system (x, y, z) be defined as shown in FIG. 6(a). FIG. 6(b) shows the view from of the locator planes looking down along the z-axis. The top edge of the planes, A, B, and C, correspond to, OU, SV and TW, respectively. Let the lines of intersection correspond to points, P, Q, and R. Using the method outlined in the pseudo-code, the distances OP, OQ, SQ, SR, TR, and TP are estimated by using cross-correlation. Let OP=a1, OQ=a2, SQ=b1, SR=b2, TR=c1, and TP=c2. Let the width of each locator plane, OU=SV=TW=d. Then:

$$O'=[0,0,0] \quad (2)$$

$$U'=[0,d,0] \quad (3)$$

$$S'=[-b1^*\sin\theta, a2+b1^*\cos\theta, 0] \quad (4)$$

$$V'=[(d-b1)^*\sin\theta, a2-(d-b1)^*\cos\theta, 0] \quad (5)$$

$$T'=[c2^*\sin\beta, a1+c2^*\cos\beta, 0] \quad (6)$$

$$W'=[-(d-c2)^*\sin\theta, a1-(d-c2)^*\cos\beta, 0] \quad (7)$$

where $$\cos\theta=(a^2+b^2-c^2)/2ab$$

$$\cos\beta=(c^2+a^2-b^2)/2ca$$

$$a=a2-a1, b=b2-b1, \text{ and } c=c2-c1.$$

Similarly, the bottom corners of the locator planes, A, B, and C, correspond to:

$$O'=[0,0,h] \quad (2)$$

$$U'=[0,d,h] \quad (3)$$

$$S'=[-b1^*\sin\theta, a2+b1^*\cos\theta, h] \quad (4)$$

$$V'=[(d-b1)^*\sin\theta, a2-(d-b1)^*\cos\theta, h] \quad (5)$$

$$T'=[c2^*\sin\beta, a1+c2^*\cos\beta, h] \quad (6)$$

$$W'=[-(d-c2)^*\sin\theta, a1-(d-c2)^*\cos\beta, h] \quad (7)$$

respectively, where h is the height of the locator plane. Therefore, the 3-D coordinates of the corner points of the three locator planes can be computed. In FIG. 7(c), each imaging plane and the two locator planes, B and C, form a triangular prism similar to the one considered above. Therefore, the corner points of each imaging plane can also be computed in the same coordinate system. Once the location of each imaging plane is known, the resulting acoustic 3-D data set is scan converted in a regular 3-D grid by using interpolation. The interpolation can use a linear algorithm or a higher order polynomial algorithm, such as a Gaussian least squares algorithm. The scan conversion step performs the same function as the scan converter 110 in FIG. 1. The method can also be readily extended to the scanning protocol shown in FIGS. 3(a) and 3(b), and other scanning protocols shown in FIGS. 7(a) and 7(b).

Scanning Protocols

Figure 7A:
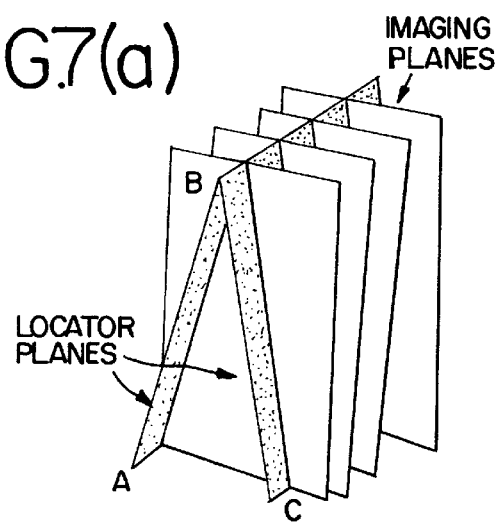
FIG. 7($a$) is a perspective view of an alternative scanning protocol with three non-coplanar locator planes (A, B, and C) and the movement of a transducer along its elevation direction.
Figure 7B:
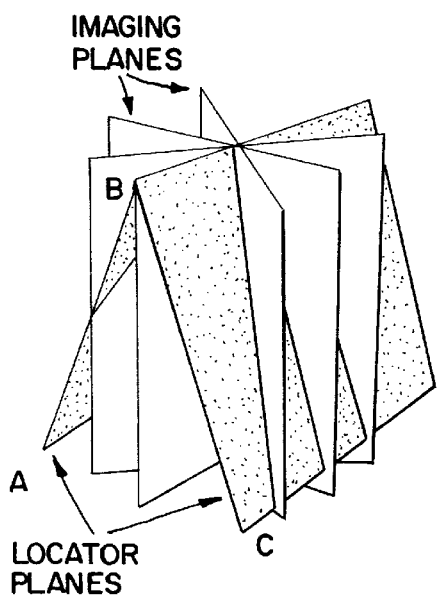
Figure 7C:
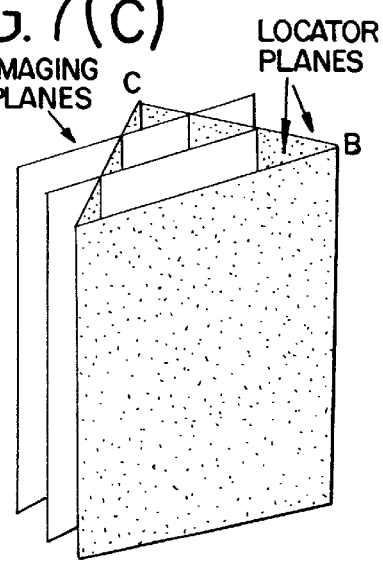

FIG. 7(a) is a perspective view of three non-coplanar locator planes (A, B, and C) and the movement of an ultrasound transducer along its elevation direction, used in an alternative scanning protocol. FIG. 7(b) is a perspective view of three non-coplanar locator planes (A, B, and C) and the rotation of an ultrasound transducer around its axial direction, used in another scanning protocol. FIG. 7(c) is a perspective view of three non-coplanar locator planes (A, B, and C) forming a triangular prism and the movement of an ultrasound transducer along its elevation direction, used in yet another scanning protocol.

FIG. 8 is a flowchart of the method used for the scanning protocol 800 for FIGS. 3(a) and 3(b). The protocol begins with step 802 in which an ultrasound transducer is positioned substantially perpendicular to the skin over the region to be scanned. Step 804 involves moving the transducer along the elevation direction and acquiring a series of 2-D data sets. Step 806 involves rotating the transducer approximately 90 degrees around its axial direction. Step 808 involves moving the transducer along its elevation direction and acquiring a second series of 2-D data sets of the same volume covered by step 804. Step 810 involves registering the 2-D data sets in 3-D. Step 810 further consists of step 812 wherein the LOI is found between each 2-D data set in step 804 and each 2-D data set in step 808; and step 814 wherein the LOIs are used to assemble all 2-D data sets into a 3-D data set. Step 816 involves scan converting the 3-D data set in a 3-D grid. Step 818 involves sending the 3-D grid data to a rendering or visualization tool. Examples of such tools are "3D Viewnix™" from the University of Pennsylvania, "Analyze™" from the Mayo Clinic in Rochester, Minn., and "EchoView™" from TomTec Inc. in Munich, Germany.

Figure 9:
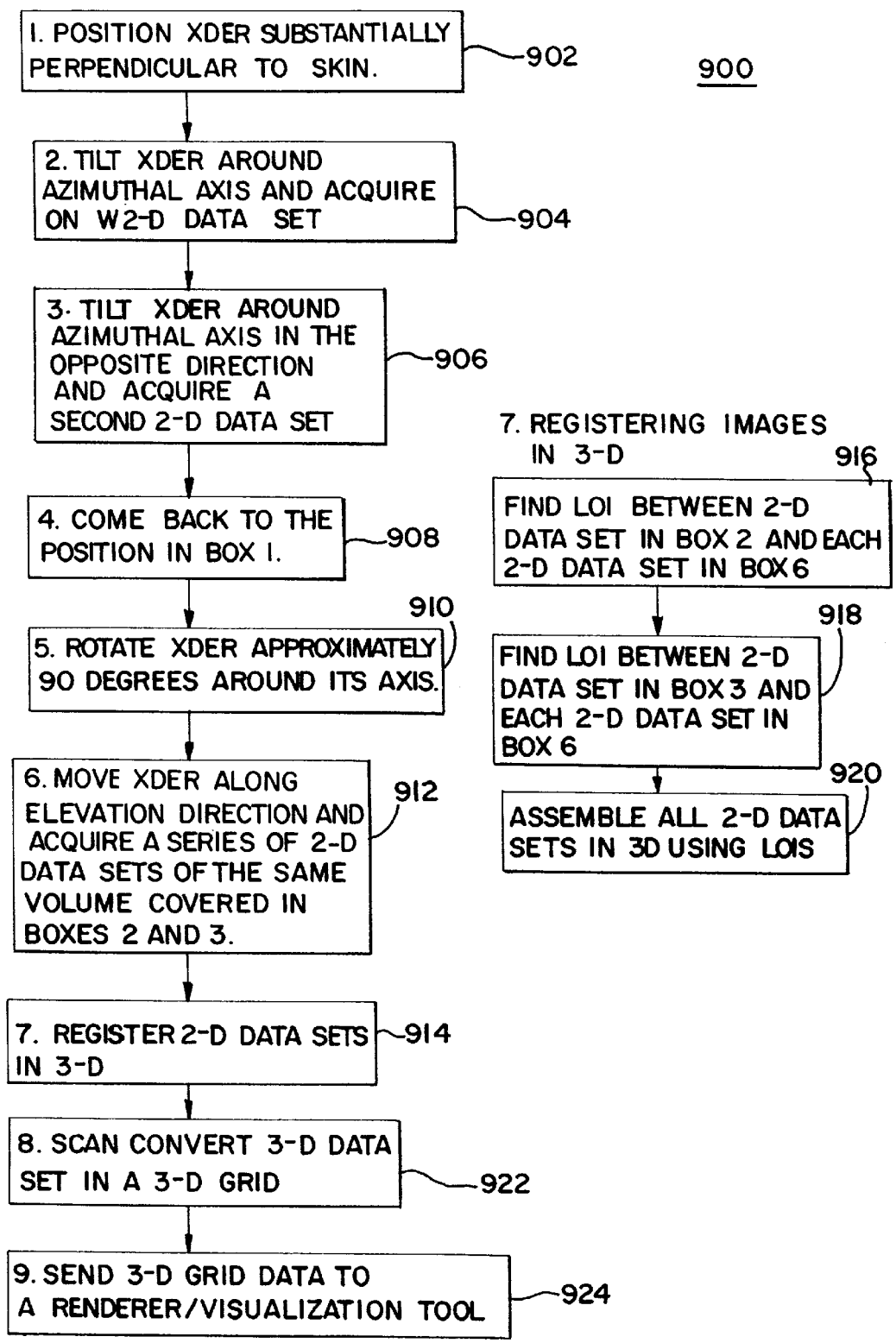
FIG. 9 is a flowchart of the method used for the scanning protocol for FIG. 7($a$).

FIG. 9 is a flowchart of the method used for the scanning protocol 900 for FIG. 7(a). The protocol begins with step 902 in which an ultrasound transducer is positioned substantially perpendicular to the skin over the region to be scanned. Step 904 involves tilting the transducer around its azimuthal axis and acquiring one 2-D data set. Step 906 involves tilting the transducer around its azimuthal axis in the opposite direction and acquiring a second 2-D data set. Step 908 involves coming back to the position in step 902. Step 910 involves rotating the transducer approximately 90 degrees on its axial direction. Step 912 involves moving the transducer along its elevation direction and acquiring a series of 2-D data sets of the same volume covered by the 2-D data sets from steps 904 and 906. Step 914 involves registering the 2-D data sets in 3-D. Step 914 further consists of step 916 wherein the LOI is found between the 2-D data set in step 904 and each 2-D data set in step 912; step 918 wherein the LOI is found between the 2-D data set in step 906 and each 2-D data set in step 912; and step 920 wherein all the 2-D data sets are assembled in 3-D using LOIs. Step 922 involves scan converting the 3-D data set in a 3-D grid. Step 924 involves sending the 3-D grid data to a rendering or visualization tool.

Figure 10:
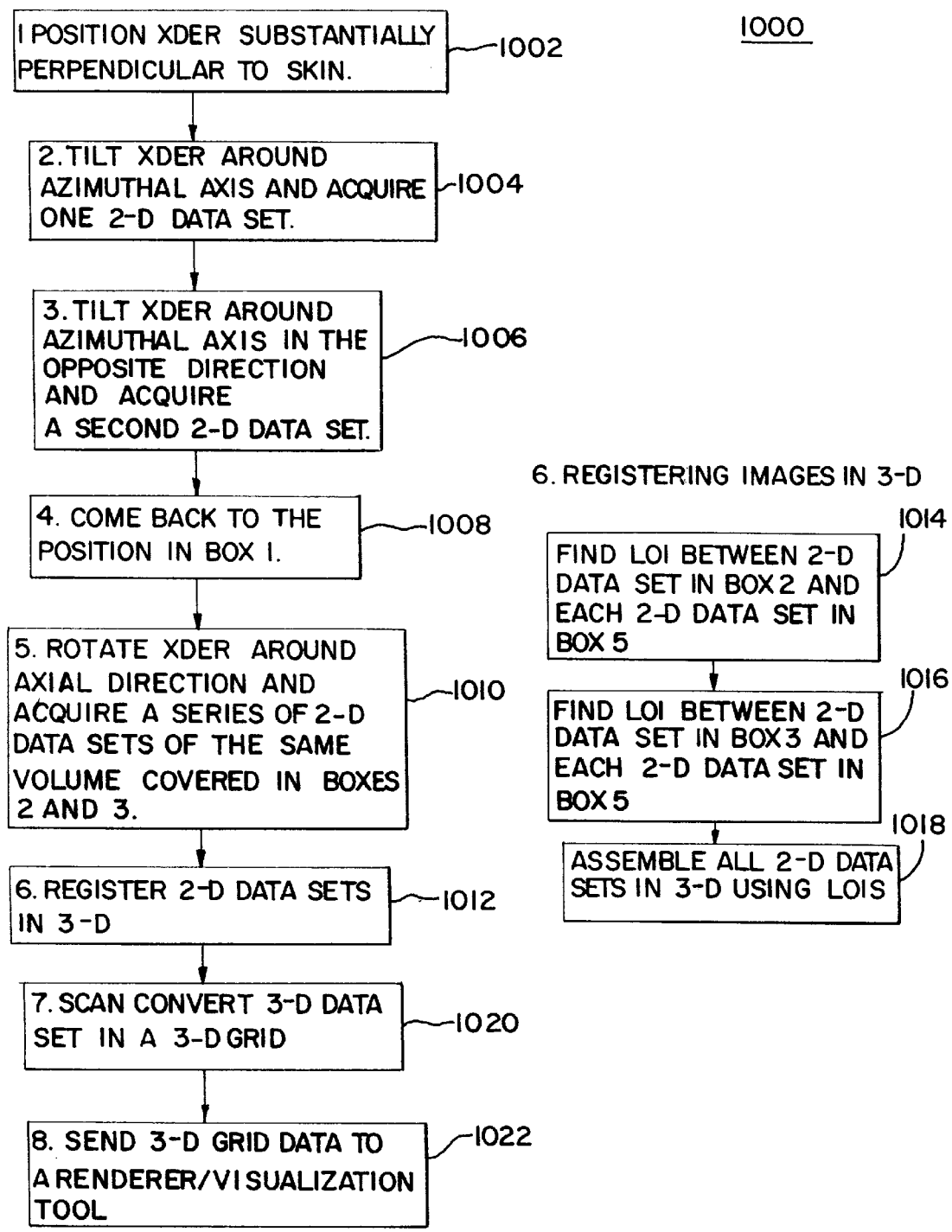
FIG. 10 is a flowchart of the method used for the scanning protocol for FIG. 7($b$).

FIG. 10 is a flowchart of the method used for the scanning protocol 1000 for FIG. 7(b). The protocol begins with step 1002 in which an ultrasound transducer is positioned substantially perpendicular to the skin over the region to be scanned. Step 1004 involves tilting the transducer around its azimuthal axis and acquiring one 2-D data set. Step 1006 involves tilting the transducer around its azimuthal axis in the opposite direction and acquiring a second 2-D data set. Step 1008 involves coming back to the position in step 1002. Step 1010 involves rotating the transducer around its axial direction and acquiring a series of 2-D data sets of the same volume covered by the 2-D data sets from steps 1004 and 1006. Step 1012 involves registering the 2-D data sets in 3-D. Step 1012 further consists of step 1014 wherein the LOI is found between the 2-D data set in step 1004 and each 2-D data set in step 1010; step 1016 wherein the LOI is found between the 2-D data set in step 1006 and each 2-D data set in step 1010; and step 1018 wherein all the 2-D data sets are assembled in 3-D using LOIs. Step 1020 involves scan converting the 3-D data set in a 3-D grid. Step 1022 involves sending the 3-D grid data to a rendering or visualization tool.

FIG. 11 is a flowchart of the method used for the scanning protocol 1100 for FIG. 7(c). The protocol begins with step 1102 which involves positioning an ultrasound transducer substantially perpendicular to the skin over the region to be scanned and acquiring a first 2-D data set. Step 1104 involves rotating the transducer at one end around its axial direction approximately 60 degrees and acquiring a second 2-D data set. Step 1106 involves rotating the transducer at one end around its axial direction approximately 60 degrees in the same rotational direction in step 1104 and acquiring a third 2-D data set, such that the transducer position is rotated approximately 60 degrees to the transducer position in step 1102. Step 1108 involves moving the transducer along its elevation direction and acquiring a series of 2-D data sets of the same volume covered by steps 1102, 1104, and 1106. Step 1110 involves registering the 2-D data sets in 3-D. Step 1110 further consists of step 1112 wherein the LOI is found between each 2-D data set in steps 1102 and 1104; step 1114 wherein the LOI is found between each 2-D data set in steps 1104 and 1106; step 1116 wherein the LOI is found between each 2-D data set in steps 1106 and 1102; step 1118 wherein the LOI is found between each 2-D data set in steps 1102 and 1108; step 1120 wherein the LOI is found between each 2-D data set in steps 1104 and 1108; and step 1122 wherein the LOIs are used to assemble all 2-D data sets in 3-D. Step 1124 involves scan converting the 3-D data set in a 3-D grid. Step 1126 involves sending the 3-D grid data to a rendering or visualization tool.

The scanning in all protocols is preferably performed in a window of time with separate physiological signal (e.g., cardiac or respiratory signal) gating or with gating from a combination of signals. The cardiac gating is preferably implemented by inputting cardiac signals into a computer-readable port. The respiratory gating is preferably implemented by inputting electrical signals generated from respiration into a computer-readable port.

In the above description, a linear scan format was assumed for simplicity. Other scan formats, such as sector, Vector® wide view, curvilinear or curved Vector® wide view, can also be used in a similar fashion when using the scan- converted data. However, when using acoustic data, the above pseudo-code may need to be modified in some cases as follows.

For the sector scan format, the line origin1 and origin2 are constant for all iterations. For the Vector® wide view scan format, the original pseudo-code can be used as it is. The pseudo-code for the curvilinear and curved Vector® wide view scan formats are similar to the sector and Vector® wide view scan formats, except that a line-dependent sample offset should be pre-appended to each line of data.

Not all scanning protocols described above are applicable to all scan formats. Furthermore, new protocols not herein described may also be applicable to these scan formats as well.

The exemplary embodiments described herein are for purposes of illustration and are not intended to be limiting. For example, while specific hardware and software implementations are noted herein, it will be appreciated that the invention involves calculations that can be performed either in hardware or in software (i.e., a computer program embodied on an electronically-readable medium), depending on the constraints of time and cost. Furthermore, the blocks shown in FIGS. 1 and 2 are illustrative and not limiting. Many other configurations of these blocks are possible, and the broadest scope of the invention would permit many of the blocks to be omitted. Therefore, those skilled in the art will recognize that other embodiments could be practiced without departing from the scope and spirit of the claims set forth below.

What is claimed is:

1. A method for medical ultrasound imaging to generate a 3-D volume of data from a human or animal, the method comprising the acts of:
    (a) determining a line of intersection for at least a pair of intersecting 2-D data sets; and
    (b) assembling the two intersecting 2-D data sets into a 3-D data set wherein the position of the 2-D data sets within the 3-D data set is a function of the line of intersection.

2. The method of claim 1, wherein act (a) further comprises finding the line of intersection that maximizes the cross-correlation coefficient of samples of data from a plurality of possible pairs of lines within the 2-D data sets.

3. The method of claim 1, wherein act (a) further comprises finding the line of intersection that maximizes the product of samples of data from a plurality of possible pairs of lines within the 2-D data sets.

4. The method of claim 1, wherein act (a) further comprises finding the line of intersection that minimizes the sum of absolute differences of samples of data from a plurality of possible pairs of lines within the 2-D data sets.

5. The method of claim 1, wherein act (a) further comprises finding the line of intersection that minimizes the sum of squared differences of samples of data from a plurality of possible pairs of lines within the 2-D data sets.

6. The method of claim 1, wherein the lines of data are determined by combining a plurality of adjacent raw complex number samples of pre-detection data.

7. The method of claim 1, wherein a line of intersection is determined by two or more points.

8. The method of claim 1, wherein a line of intersection is determined by at least one line segment.

9. The method of claim 1, further comprising the act of acquiring the plurality of 2-D data sets in a window of time gated by a physiological signal.

10. The method of claim 1, wherein the 2-D and 3-D data sets are acoustic data sets and the method further comprises the act: (c) scan converting the 3-D data set to produce a 3-D grid of image data.

11. The method of claim 10, further comprising the act of:
    (d) sending the 3-D grid of image data to a rendering or visualization tool.

12. The method of claim 1, wherein the 2-D and 3-D data sets are image data sets.

13. The method of claim 12, wherein act (a) further comprises finding the line of intersection between two image data sets by maximizing the cross-correlation coefficient or the product of ultrasound line data from the image data sets, or by minimizing the sum of squared differences or sum of absolute differences of the ultrasound line data.

14. The method of claim 1, wherein the 2-D data sets include harmonic imaging data.

15. A method for medical ultrasound imaging to generate a 3-D volume of data from a human or animal, comprising the acts of:
   storing a first plurality of 2-D acoustic data sets while a 1-D transducer is moved along its elevation direction;
   storing a second plurality of 2-D acoustic data sets while the 1-D transducer is moved along its elevation direction after changing its position and orientation;
   determining a line of intersection for at least one pair of 2-D acoustic data sets from the first plurality and the second plurality of 2-D acoustic data sets; and
   assembling at least one pair of 2-D acoustic data sets from the first plurality and the second plurality of 2-D acoustic data sets into a 3-D data-set.

16. The method of claim 15, wherein the act of finding the line of intersection maximizes the cross-correlation coefficient of samples of acoustic data from a plurality of possible pairs of lines within the 2-D acoustic data sets.

17. The method of claim 15, wherein the act of finding the line of intersection maximizes the product of samples of acoustic data from a plurality of possible pairs of lines within the 2-D acoustic data sets.

18. The method of claim 15, wherein the act of finding the line of intersection minimizes the sum of absolute differences of samples of acoustic data from a plurality of possible pairs of lines within the 2-D acoustic data sets.

19. The method of claim 15, wherein the act of finding the line of intersection minimizes the sum of squared differences of samples of acoustic data from a plurality of possible pairs of lines within the 2-D acoustic data sets.

20. The method of claim 15, wherein a line of intersection is determined by combining a plurality of adjacent raw complex number samples of pre-detection data.

21. The method of claim 15, wherein a line of intersection is determined by two or more points.

22. The method of claim 15, wherein a line of intersection is determined by at least one line segment.

23. The method of claim 15, further comprising the act of acquiring the plurality of 2-D data sets in a window of time gated by a physiological signal.

24. The method of claim 15, wherein the 2-D and 3-D data sets are acoustic data sets and the method further comprises the act of scan converting the 3-D data set to produce a 3-D grid of image data.

25. The method of claim 24, further comprising the act of sending the 3-D grid of image data to a rendering or visualization tool.

26. The method of claim 15, wherein the 2-D and 3-D data sets are image data sets.

27. The method of claim 26, wherein the act of determining the line of intersection further comprises finding the line of intersection between two image data sets by maximizing the cross-correlation coefficient or the product of ultrasound line data from the image data sets, or by minimizing the sum of squared differences or sum of absolute differences of the ultrasound line data.

28. The method of claim 15, wherein the 2-D data sets include harmonic imaging data.

29. A method for medical ultrasound imaging to generate a 3-D volume of acoustic data obtained by using a 1-D ultrasound transducer, comprising the acts of:
   storing a first plurality of 2-D acoustic data sets to generate locator planes while the 1-D ultrasound transducer is moved into non-coplanar planes;
   storing a second plurality of 2-D acoustic data sets while the 1-D ultrasound transducer is moved along its elevation direction;
   determining a line of intersection for at least one pair of 2-D acoustic data sets from the first plurality and the second plurality of 2-D acoustic data sets; and
   assembling at least one pair of 2-D acoustic data sets from the first plurality and the second plurality of 2-D acoustic data sets into a 3-D data-set.

30. The method of claim 29, wherein the act of finding the line of intersection maximizes the cross-correlation coefficient of samples of acoustic data from a plurality of possible pairs of lines within the 2-D acoustic data sets.

31. The method of claim 29, wherein the act of finding the line of intersection maximizes the product of samples of acoustic data from a plurality of possible pairs of lines within the 2-D acoustic data sets.

32. The method of claim 29, wherein the act of finding the line of intersection minimizes the sum of absolute differences of samples of acoustic data from a plurality of possible pairs of lines within the 2-D acoustic data sets.

33. The method of claim 29, wherein act of finding the line of intersection minimizes the sum of squared differences of samples of acoustic data from a plurality of possible pairs of lines within the 2-D acoustic data sets.

34. The method of claim 29, wherein a line of intersection is determined by combining a plurality of adjacent raw complex number samples of pre-detection data.

35. The method of claim 29, wherein a line of intersection is determined by two or more points.

36. The method of claim 29, wherein a line of intersection is determined by at least one line segment.

37. The method of claim 29, further comprising the act of acquiring the plurality of 2-D data sets in a window of time gated by a physiological signal.

38. The method of claim 29, wherein the 2-D and 3-D data sets are acoustic data sets and the method further comprises the act of scan converting the 3-D data set to produce a 3-D grid of image data.

39. The method of claim 38, further comprising the act of sending the 3-D grid of image data to a rendering or visualization tool.

40. The method of claim 29, wherein the 2-D and 3-D data sets are image data sets.

41. The method of claim 40, wherein the act of determining the line of intersection further comprises finding the line of intersection between two image data sets by maximizing the cross-correlation coefficient or the product of ultrasound line data from the image data sets, or by minimizing the sum of squared differences or sum of absolute differences of the ultrasound line data.

42. The method of claim 29, wherein the 2-D data sets include harmonic imaging data.

43. A method for medical ultrasound imaging to generate a 3-D volume of data from a human or animal, comprising the acts of:
   storing a first plurality of 2-D acoustic data sets to generate locator planes while the 1-D ultrasound transducer is moved into non-coplanar planes;
   storing a second plurality of 2-D acoustic data sets while the 1-D ultrasound transducer is rotated substantially 180 degrees around its central axis;
   determining a line of intersection for at least one pair of 2-D acoustic data sets from the first plurality and the second plurality of 2-D acoustic data sets; and assembling at least one pair of 2-D acoustic data sets from the first plurality and the second plurality of 2-D ultrasound data sets into a 3-D data-set.

44. The method of claim 43, wherein the act of finding the line of intersection maximizes the cross-correlation coefficient of samples of acoustic data from a plurality of possible pairs of lines within the 2-D acoustic data sets.

45. The method of claim 43, wherein the act of finding the line of intersection maximizes the product of samples of acoustic data from a plurality of possible pairs of lines within the 2-D acoustic data sets.

46. The method of claim 43, wherein the act of finding the line of intersection minimizes the sum of absolute differences of samples of acoustic data from a plurality of possible pairs of lines within the 2-D acoustic data sets.

47. The method of claim 43, wherein act of finding the line of intersection minimizes the sum of squared differences of samples of acoustic data from a plurality of possible pairs of lines within the 2-D acoustic data sets.

48. The method of claim 43, wherein a line of intersection is determined by combining a plurality of adjacent raw complex number samples of pre-detection data.

49. The method of claim 43, wherein a line of intersection is determined by two or more points.

50. The method of claim 43, wherein a line of intersection is determined by at least one line segment.

51. The method of claim 43, further comprising the act of acquiring the plurality of 2-D data sets in a window of time gated by a physiological signal.

52. The method of claim 43, wherein the 2-D and 3-D data sets are acoustic data sets and the method further comprises the step of scan converting the 3-D data set to produce a 3-D grid of image data.

53. The method of claim 52, further comprising the act of sending the 3-D grid of image data to a rendering or visualization tool.

54. The method of claim 43, wherein the 2-D and 3-D data sets are image data sets.

55. The method of claim 54, wherein the act of determining the line of intersection further comprises finding the line of intersection between two image data sets by maximizing the cross-correlation coefficient or the product of ultrasound line data from the image data sets, or by minimizing the sum of squared differences or sum of absolute differences of the ultrasound line data.

56. The method of claim 43, wherein the 2-D data sets include harmonic imaging data.

57. A method for medical ultrasound imaging to generate a 3-D volume of data from a human or animal, comprising the acts of:
storing a first plurality of 2-D acoustic data sets to generate locator planes while a 1-D ultrasound transducer is moved to obtain a 2-D ultrasound data set of three mutually intersecting planes in a triangular prism;
storing a second plurality of 2-D acoustic data sets while the 1-D ultrasound transducer is moved along its elevation direction;
determining the line of intersection for at least one pair of 2-D acoustic data sets from the first plurality and the second plurality of 2-D acoustic data sets; and
assembling at least one pair of 2-D acoustic data sets from the first plurality and the second plurality of 2-D acoustic data sets into a 3-D data-set.

58. The method of claim 57, wherein the act of finding the line of intersection maximizes the cross-correlation coefficient of samples of acoustic data from a plurality of possible pairs of lines within the 2-D acoustic data sets.

59. The method of claim 57, wherein the act of finding the line of intersection maximizes the product of samples of acoustic data from a plurality of possible pairs of lines within the 2-D acoustic data sets.

60. The method of claim 57, wherein the act of finding the line of intersection minimizes the sum of absolute differences of samples of acoustic data from a plurality of possible pairs of lines within the 2-D acoustic data sets.

61. The method of claim 57, wherein act of finding the line of intersection minimizes the sum of squared differences of samples of acoustic data from a plurality of possible pairs of lines within the 2-D acoustic data sets.

62. The method of claim 57, wherein a line of intersection is determined by combining a plurality of adjacent raw complex number samples of pre-detection data.

63. The method of claim 57, wherein a line of intersection is determined by two or more points.

64. The method of claim 57, wherein a line of intersection is determined by at least one line segment.

65. The method of claim 57, further comprising the act of acquiring the plurality of 2-D data sets in a window of time gated by a physiological signal.

66. The method of claim 57, wherein the 2-D and 3-D data sets are acoustic data sets and the method further comprises the act of scan converting the 3-D data set to produce a 3-D grid of image data.

67. The method of claim 66, further comprising the act of sending the 3-D grid of image data to a rendering or visualization tool.

68. The method of claim 57, wherein the 2-D and 3-D data sets are image data sets.

69. The method of claim 68, wherein act of determining the line of intersection further comprises finding the line of intersection between two image data sets by maximizing the cross-correlation coefficient or the product of ultrasound line data from the image data sets, or by minimizing the sum of squared differences or sum of absolute differences of the ultrasound line data.

70. The method of claim 57, wherein the 2-D data sets include harmonic imaging data.

71. A medical ultrasound imaging system to generate data for constructing a 3-D volume of data from a human or animal, comprising:
(a) means for determining, for at least one non-parallel pair of 2-D data sets, a line of intersection; and
(b) means for assembling a 3-D data set with the at least one pair of 2-D data sets wherein the position of the 2-D data sets within the 3-D data set is a function of the line of intersection.

72. The system of claim 71, wherein the means for finding the line of intersection maximizes the cross-correlation coefficient of samples of data from a plurality of possible pairs of lines within the 2-D data sets.

73. The system of claim 71, wherein the means for finding the line of intersection maximizes the product of samples of data from a plurality of possible pairs of lines within the 2-D data sets.

74. The system of claim 71, wherein the means for finding the line of intersection minimizes the sum of absolute differences of samples of data from a plurality of possible pairs of lines within the 2-D data sets.

75. The system of claim 71, wherein the means for finding the line of intersection minimizes the sum of squared differences of samples of data from a plurality of possible pairs of lines within the 2-D data sets.

76. The system of claim 71, wherein a line of intersection is determined by combining a plurality of adjacent raw complex number samples of pre-detection data.

77. The system of claim 71, wherein a line of intersection is determined by two or more points.

78. The system of claim 71, wherein a line of intersection is determined by at least one line segment.

79. The system of claim 71, further comprising means for acquiring the plurality of 2-D data sets in a window of time gated by a physiological signal.

80. The system of claim 71, wherein the 2-D and 3-D data sets are acoustic data sets and the system further comprises means for scan converting the 3-D data set to produce a 3-D grid of image data.

81. The system of claim 80, further comprising means for sending the 3-D grid of image data to a rendering or visualization tool.

82. The system of claim 71, wherein the 2-D and 3-D data sets are image data sets.

83. The system of claim 82, further comprising means for finding the line of intersection between two image data sets by maximizing the cross-correlation coefficient or the product of ultrasound line data from the image data sets, or by minimizing the sum of squared differences or sum of absolute differences of the ultrasound line data.

84. The system of claim 71, wherein the 2-D data sets include harmonic imaging data.

85. A computer program embodied on an electronically-readable medium, for medical ultrasound imaging to generate a 3-D volume of data from a human or animal, comprising code for:

imputing a first plurality of 2-D data sets;

inputting a second plurality of 2-D data sets after a 1-D ultrasound transducer changes its position and orientation;

determining, for at least one non-parallel pair of 2-D data sets, a line of intersection; and assembling a 3-D data set with the at least one pair of 2-D data sets wherein the position of the 2-D data sets within the 3-D data set is a function of the line of intersection.

86. The computer program of claim 85, wherein the code for finding the line of intersection maximizes the cross-correlation coefficient of samples of data from a plurality of possible pairs of lines within the 2-D data sets.

87. The computer program of claim 85, wherein the code for finding the line of intersection maximizes the product of samples of data from a plurality of possible pairs of lines within the 2-D data sets.

88. The computer program of claim 85, wherein the code for finding the line of intersection minimizes the sum of absolute differences of samples of data from a plurality of possible pairs of lines within the 2-D data sets.

89. The computer program of claim 85, wherein the code for finding the line of intersection minimizes the sum of squared differences of samples of data from a plurality of possible pairs of lines within the 2-D data sets.

90. The computer program of claim 85, wherein the lines of data are determined by combining a plurality of adjacent raw complex number samples of pre- detection data.

91. The computer program of claim 85, wherein a line of intersection is determined by two or more points.

92. The computer program of claim 85, wherein a line of intersection is determined by at least one line segment.

93. The computer program of claim 85, further comprising code for acquiring the plurality of 2-D data sets in a window of time gated by a physiological signal.

94. The computer program of claim 85, wherein the 2-D and 3-D data sets are acoustic data sets and the computer program further comprises code for scan converting the 3-D data set to produce a 3-D grid of image data.

95. The computer program of claim 94, further comprising code for sending the 3-D grid of image data to a rendering or visualization tool.

96. The computer program of claim 85, wherein the 2-D and 3-D data sets are image data sets.

97. The computer program of claim 96, wherein the code for determining a line of intersection further comprises code for finding the line of intersection between two image data sets by maximizing the cross-correlation coefficient or the product of ultrasound line data from the image data sets, or by minimizing the sum of squared differences or sum of absolute differences of the ultrasound line data.

98. The computer program of claim 85, wherein the 2-D data sets include harmonic imaging data.

99. A computer program embodied on an electronically-readable medium, for medical ultrasound imaging to generate a 3-D volume of data from a human or animal, comprising code for:

imputing a first plurality of 2-D data sets to generate locator planes;

inputting a second plurality of 2-D data sets;

determining, for at least one non-parallel pair of 2-D data sets, a line of intersection; and assembling a 3-D data set with the at least one pair of 2-D data sets wherein the position of the 2-D data sets within the 3-D data set is a function of the line of intersection.

100. The computer program of claim 99, wherein the code for finding the line of intersection maximizes the cross-correlation coefficient of samples of data from a plurality of possible pairs of lines within the 2-D data sets.

101. The computer program of claim 99, wherein the code for finding the line of intersection maximizes the product of samples of data from a plurality of possible pairs of lines within the 2-D data sets.

102. The computer program of claim 99, wherein the code for finding the line of intersection minimizes the sum of absolute differences of samples of data from a plurality of possible pairs of lines within the 2-D data sets.

103. The computer program of claim 99, wherein the code for finding the line of intersection minimizes the sum of squared differences of samples of data from a plurality of possible pairs of lines within the 2-D data sets.

104. The computer program of claim 99, wherein the lines of data are determined by combining a plurality of adjacent raw complex number samples of pre-detection data.

105. The computer program of claim 99, wherein a line of intersection is determined by two or more points.

106. The computer program of claim 99, wherein a line of intersection is determined by at least one line segment.

107. The computer program of claim 99, further comprising code for acquiring the plurality of 2-D data sets in a window of time gated by a physiological signal.

108. The computer program of claim 99, wherein the 2-D and 3-D data sets are acoustic data sets and the computer program further comprises code for scan converting the 3-D data set to produce a 3-D grid of image data.

109. The computer program of claim 108, further comprising code for sending the 3-D grid of image data to a rendering or visualization tool.

110. The computer program of claim 99, wherein the 2-D and 3-D data sets are image data sets.

111. The computer program of claim 110, wherein the code for finding the line of intersection further comprises code for finding the line of intersection between two image data sets by maximizing the cross-correlation coefficient or the product of ultrasound line data from the image data sets, or by minimizing the sum of squared differences or sum of absolute differences of the ultrasound line data.

112. The computer program of claim 99, wherein the 2-D data sets include harmonic imaging data.

* * * * *

UNITED STATES PATENT AND TRADEMARK OFFICE
CERTIFICATE OF CORRECTION

PATENT NO. : 6,234,968 B1
DATED : May 22, 2001
INVENTOR(S) : T. S. Sumanaweera et al.

It is certified that error appears in the above-identified patent and that said Letters Patent is hereby corrected as shown below:

<u>Title page,</u>
Item [56], U.S. PATENT DOCUMENTS, delete "2/1998" and substitute -- 2/1994 -- in its place.

<u>Column 7,</u>
Line 32, equation (2), delete "O' " and substitute -- O -- in its place.
Line 33-1/2, equation (3), delete "U' " and substitute -- U -- in its place.
Line 35, equation (4), delete "S' " and substitute -- S -- in its place.
Line 37, equation (5), delete "V'" and substitute -- V -- in its place.
Line 38-1/2, equation (6), delete "T' " and substitute -- T -- in its place.
Line 40, equation (7), delete "sin θ" and substitute -- sin β -- in its place.
Line 61, equation (7), delete "sin θ" and substitute -- sin β -- in its place.

Signed and Sealed this

Tenth Day of September, 2002

Attest:

Attesting Officer

JAMES E. ROGAN
Director of the United States Patent and Trademark Office